United States Patent
Noonan et al.

(10) Patent No.: US 10,357,323 B2
(45) Date of Patent: Jul. 23, 2019

(54) SYSTEM AND METHOD FOR MINIMIZING TWIST FOR OPTICAL SHAPE SENSING ENABLED INSTRUMENTS

(71) Applicant: KONINKLIJKE PHILIPS N.V., Eindhoven (NL)

(72) Inventors: David Paul Noonan, New York, NY (US); Raymond Chan, San Diego, CA (US); Molly Lara Flexman, New York, NY (US); Bharat Ramachandran, Morganville, NJ (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 965 days.

(21) Appl. No.: 14/771,039

(22) PCT Filed: Mar. 26, 2014

(86) PCT No.: PCT/IB2014/060159
§ 371 (c)(1),
(2) Date: Aug. 27, 2015

(87) PCT Pub. No.: WO2014/155303
PCT Pub. Date: Oct. 2, 2014

(65) Prior Publication Data
US 2016/0008089 A1 Jan. 14, 2016

Related U.S. Application Data

(60) Provisional application No. 61/805,194, filed on Mar. 26, 2013.

(51) Int. Cl.
*A61B 34/20* (2016.01)
*A61B 34/00* (2016.01)
(Continued)

(52) U.S. Cl.
CPC .............. *A61B 34/76* (2016.02); *A61B 34/20* (2016.02); *A61B 34/30* (2016.02);
(Continued)

(58) Field of Classification Search
CPC .. A61B 34/20; A61B 34/30; A61B 2034/2061
See application file for complete search history.

(56) References Cited

U.S. PATENT DOCUMENTS

| 8,818,143 B2 | 8/2014 | Younge et al. |
| 2011/0021926 A1 | 1/2011 | Spencer et al. |

(Continued)

FOREIGN PATENT DOCUMENTS

| CN | 101732027 A | 6/2010 |
| JP | 2008173395 A | 7/2008 |

*Primary Examiner* — Nathan J Jenness

(57) ABSTRACT

A shape sensing system includes a guide tube (304) and an optical shape sensing device (104) including one or more optical fibers and being proximally fixed at a fixation point and being disposed within the guide tube. An interventional instrument (102) is rigidly attached to a handle (212) to prevent rotation of the instrument relative to the handle. The instrument has a lumen configured to receive the guide tube therein such that the optical shape sensing device is unconstrained throughout the instrument and the handle, and the guide tube is free to slip relative to at least rotation of the instrument and the handle without transferring torsional friction to optical shape sensing device.

13 Claims, 4 Drawing Sheets

(51) Int. Cl.
*A61B 34/30* (2016.01)
*A61B 90/00* (2016.01)
*A61B 17/00* (2006.01)

(52) U.S. Cl.
CPC ............ *A61B 2017/00318* (2013.01); *A61B 2034/2061* (2016.02); *A61B 2090/0811* (2016.02); *A61B 2560/0475* (2013.01); *A61B 2560/0487* (2013.01)

(56) References Cited

U.S. PATENT DOCUMENTS

2011/0202069 A1 8/2011 Prisco et al.
2011/0319910 A1 12/2011 Roelle et al.
2012/0321243 A1 12/2012 Younge et al.

SYSTEM AND METHOD FOR MINIMIZING TWIST FOR OPTICAL SHAPE SENSING ENABLED INSTRUMENTS

CROSS-REFERENCE TO PRIOR APPLICATIONS

This application is the U.S. National Phase application under 35 U.S.C. § 371 of International Application Serial No. PCT/IB2014/060159, filed on Mar. 26, 2014, which claims the benefit of U.S. Application Ser. No. 61/805,194, filed on Mar. 26, 2013. These applications are hereby incorporated by reference herein.

BACKGROUND

Technical Field

This disclosure relates to medical instruments and more particularly to a shape sensing system with rotational constraints and/or control of optical fibers for medical applications.

Description of the Related Art

An optical shape sensing (OSS) fiber can only produce accurate shape reconstruction until about a 2π twist about its axis is reached in either direction, while losing stability close to 6π of cumulative twist. This is due to reconstruction algorithms which compare the signal in three outer cores to a central (no twist) core, and excessive twist along the longitudinal axis of the fiber limits the ability to differentiate phase differences due to bending versus other factors.

Twist can be introduced by an operator while applying a torque to the instrument or to the handle of the instrument as it is manipulated or, by friction between the fiber and the instrument lumen as the instrument is moved. For clinical use, specifically in vascular procedures, surgeons often torque the instrument through multiple π turns, usually in the same direction. The amount of twist which is imparted onto the fiber by the clinician needs to be minimized, while ensuring that the instrument can still be operated and torqued in the usual manner.

SUMMARY

In accordance with the present principles, a shape sensing system includes a guide tube and an optical shape sensing device including one or more optical fibers and being proximally fixed at a fixation point and being disposed within the guide tube. An interventional instrument is rigidly attached to a handle to prevent rotation of the instrument relative to the handle. The instrument has a lumen configured to receive the guide tube therein such that the optical shape sensing device is unconstrained throughout the instrument and the handle, and the guide tube is free to slip relative to at least rotation of the instrument and the handle without transferring torsional friction to the optical shape sensing device.

Another shape sensing system includes a workstation having a processor and memory, the memory storing a shape sensing module configured to interpret optical shape sensing signals during an interventional procedure. A launch unit includes an optical fixation point for sending and receiving optical signals. A guide tube is proximally fixed at a mount point distally disposed from the fixation point. An optical shape sensing device includes one or more optical fibers and is proximally fixed at the fixation point and is disposed within the guide tube. An interventional instrument is rigidly attached to a handle to prevent rotation of the instrument relative to the handle. The instrument has a lumen configured to receive the guide tube therein such that the optical shape sensing device is unconstrained throughout the instrument and the handle, and the guide tube is free to slip relative to at least rotation of the instrument and the handle without transferring torsional friction to optical shape sensing device.

Yet another shape sensing system includes an optical shape sensing device, which includes one or more optical fibers and is proximally fixed at a fixation point. An interventional instrument is rigidly attached to a handle to prevent rotation of the instrument relative to the handle. The instrument has a lumen configured to receive the optical shape sensing device, which is constrained at at least one location in the instrument. A bearing is included in the handle and is configured to receive and attach to a protective tube wherein the handle is free to rotate relative to the bearing and the protective tube. The protective tube encapsulates the optical shape sensing device between a fixation position, at or near the fixation point, and the handle. A clutch is configured to engage the bearing to prevent rotation of the handle relative to the protective tube in accordance with an event.

These and other objects, features and advantages of the present disclosure will become apparent from the following detailed description of illustrative embodiments thereof, which is to be read in connection with the accompanying drawings.

BRIEF DESCRIPTION OF DRAWINGS

This disclosure will present in detail the following description of preferred embodiments with reference to the following figures wherein.

DETAILED DESCRIPTION OF EMBODIMENTS

Figure 1:
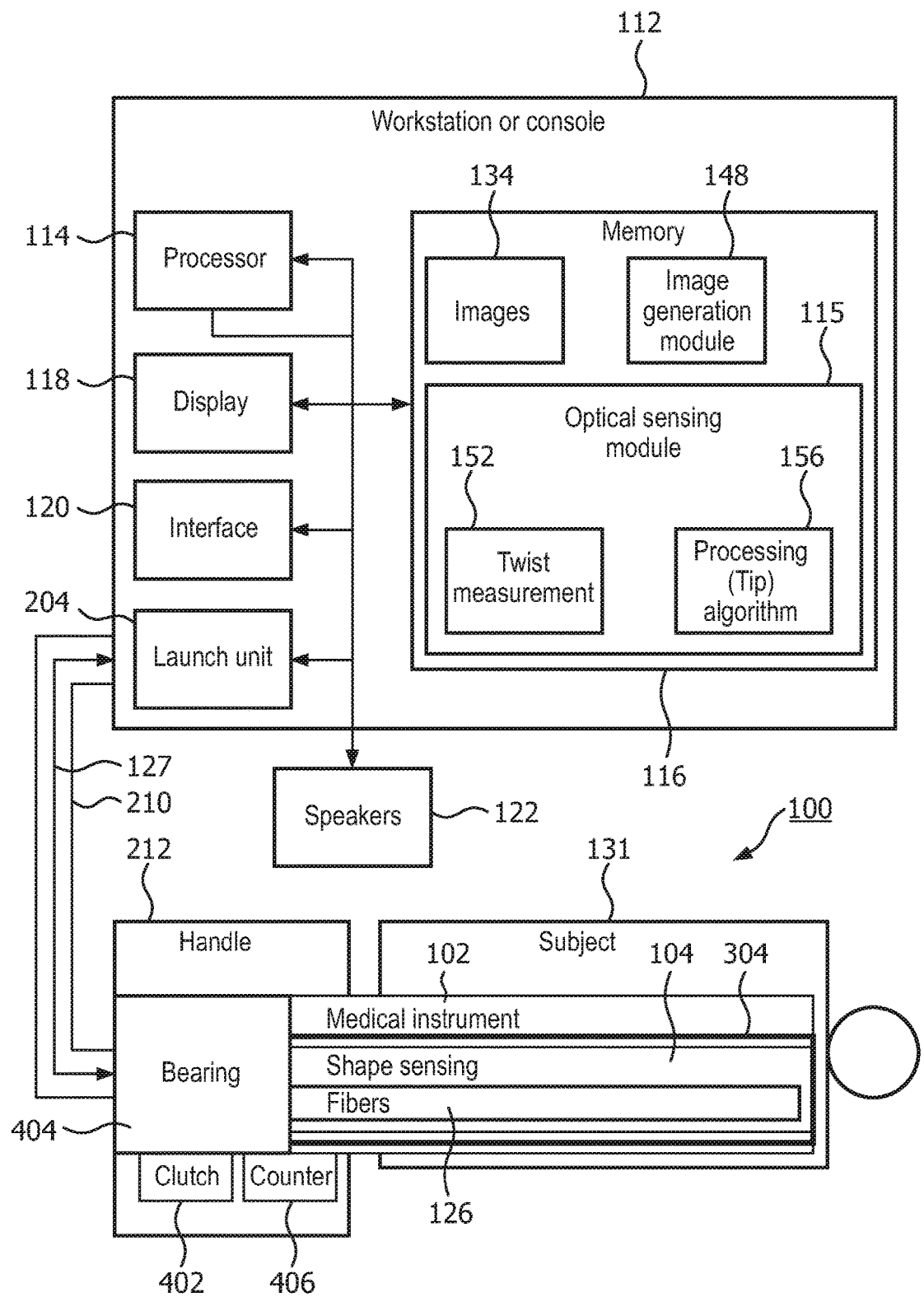
FIG. 1 is a block/flow diagram showing a shape sensing system which constrains, controls and/or limits fiber rotation in accordance with one illustrative embodiment.

In accordance with the present principles, systems and methods for mitigating over-twisting of an optical shape sensing (OSS) fiber are provided. Mechanisms for minimizing twist in OSS-enabled instruments to allow accurate and stable shape sensing are disclosed. These mechanisms mechanically isolate the OSS fiber from an interventional instrument inside a guiding tube such that the fiber is not fixed to the device at any point along its length. Simply allowing the fiber to float within the lumen of an interventional device may be insufficient to ensure stability as the device is torqued due to friction applied to the fiber by the wall of the instrument lumen as it rotates. One technique mechanically isolates the fiber from negative effects of torqueing by employing a guiding tube which essentially acts as a bearing between the instrument lumen and the fiber.

It is known that the shape reconstruction capabilities of bare OSS fibers are adversely affected by the introduction of twist along the longitudinal axis of the fiber. When testing such fibers in a controlled environment such twist can be minimized with careful handling. However, when OSS fibers are integrated into interventional instruments, such careful handling by the clinician cannot be guaranteed. In practice, a clinician will typically grasp the handle of an interventional instrument and translate it in XYZ as well as rotate it about the Z axis. Assuming that the fiber is rigidly fixed to an unmovable launch region and subsequently passes through the device handle to the distal tip of the instrument, any rotation of the handle will induce twist in the fiber. As the twist increases, the accuracy of shape reconstruction will be reduced and stability could be lost. The present principles mitigate these issues by controlling or reducing twist in the shape sensing device.

It should be understood that the present invention will be described in terms of medical instruments; however, the teachings of the present invention are much broader and are applicable to any fiber optic instruments. In some embodiments, the present principles are employed in tracking or analyzing complex biological or mechanical systems. In particular, the present principles are applicable to internal tracking procedures of biological systems, procedures in all areas of the body such as the lungs, gastro-intestinal tract, excretory organs, blood vessels, all endovascular and endoluminal applications, etc. The elements depicted in the FIGS. may be implemented in various combinations of hardware and software and provide functions which may be combined in a single element or multiple elements.

The functions of the various elements shown in the FIGS. can be provided through the use of dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor ("DSP") hardware, read-only memory ("ROM") for storing software, random access memory ("RAM"), non-volatile storage, etc.

Moreover, all statements herein reciting principles, aspects, and embodiments of the invention, as well as specific examples thereof, are intended to encompass both structural and functional equivalents thereof. Additionally, it is intended that such equivalents include both currently known equivalents as well as equivalents developed in the future (i.e., any elements developed that perform the same function, regardless of structure). Thus, for example, it will be appreciated by those skilled in the art that the block diagrams presented herein represent conceptual views of illustrative system components and/or circuitry embodying the principles of the invention. Similarly, it will be appreciated that any flow charts, flow diagrams and the like represent various processes which may be substantially represented in computer readable storage media and so executed by a computer or processor, whether or not such computer or processor is explicitly shown.

Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W), Blu-Ray™ and DVD.

Referring now to the drawings in which like numerals represent the same or similar elements and initially to FIG. 1, a system 100 for an interventional procedure using one or more optical shape sensing enabled instruments is illustratively shown in accordance with one embodiment. System 100 may include a workstation or console 112 from which a procedure is supervised and/or managed. Workstation 112 preferably includes one or more processors 114 and memory 116 for storing programs and applications. Memory 116 may store an optical sensing module 115 configured to interpret optical feedback signals from a shape sensing device or system 104. Optical sensing module 115 is configured to use the optical signal feedback (and any other feedback, e.g., electromagnetic (EM) tracking) to reconstruct deformations, deflections and other changes associated with a flexible medical device or instrument 102 and/or its surrounding region. In particular, the module 115 is configured to estimate device roll even in the case where the shape sensing device 104 is rotationally isolated from the flexible instrument 102, being rotated using a rotary bearing in the form of a guide tube 304. The guide tube 304 includes a smooth surface to reduce friction against internal surfaces of the medical instrument 102. The shape sensing device 104 is free to slip within the guide tube 304.

The medical device 102 may include a catheter, a guidewire, a probe, an endoscope, an electrode, a filter device, a balloon device, or other medical component, etc. The shape sensing system 104 in device 102 includes one or more optical fibers 126 which are coupled to the device 102 in a set pattern or patterns. The optical fibers 126 connect to the workstation 112 through cabling 127. The cabling 127 may include fiber optics, electrical connections, other instrumentation, etc., as needed.

Shape sensing system 104 with fiber optics may be based on fiber optic Bragg grating sensors. A fiber optic Bragg grating (FBG) is a short segment of optical fiber that reflects particular wavelengths of light and transmits all others. This is achieved by adding a periodic variation of the refractive index in the fiber core, which generates a wavelength-specific dielectric mirror. A fiber Bragg grating can therefore be used as an inline optical filter to block certain wavelengths, or as a wavelength-specific reflector.

A fundamental principle behind the operation of a fiber Bragg grating is Fresnel reflection at each of the interfaces where the refractive index is changing. For some wavelengths, the reflected light of the various periods is in phase so that constructive interference exists for reflection and, consequently, destructive interference for transmission. The Bragg wavelength is sensitive to strain as well as to temperature. This means that Bragg gratings can be used as sensing elements in fiber optical sensors. In an FBG sensor, the measurand (e.g., strain) causes a shift in the Bragg wavelength.

One advantage of this technique is that various sensor elements can be distributed over the length of a fiber. Incorporating three or more cores with various sensors (gauges) along the length of a fiber that is embedded in a structure permits a three dimensional form of such a structure to be precisely determined, typically with better than 1 mm accuracy. Along the length of the fiber, at various positions, a multitude of FBG sensors can be located (e.g., 3 or more fiber sensing cores). From the strain measurement of each FBG, the curvature of the structure can be inferred at that position. From the multitude of measured positions, the total three-dimensional form is determined.

As an alternative to fiber-optic Bragg gratings, the inherent backscatter in conventional optical fiber can be exploited. One such approach is to use Rayleigh scatter in standard single-mode communications fiber. Rayleigh scatter occurs as a result of random fluctuations of the index of refraction in the fiber core. These random fluctuations can be modeled as a Bragg grating with a random variation of amplitude and phase along the grating length. By using this effect in three or more cores running within a single length of multicore fiber, the 3D shape and dynamics of the surface of interest can be followed.

This shape sensing approach is to exploit the inherent backscatter in a conventional optical fiber. The principle used is distributed strain measurement in the optical fiber with characteristic Rayleigh scatter patterns, for example, in standard single-mode communications fiber. Rayleigh scatter occurs as a result of random fluctuations of the index of refraction in the fiber core. These random fluctuations can be modeled with a random variation of amplitude and phase along the length. By using this effect in 3 or more cores running within a single length of multicore fiber and monitoring changes in the phase of the backscattered signal due to strain, tension, and temperature effects relative to a calibrated reference state, the 3D shape and dynamics of the fiber sensor can be reconstructed and the corresponding shape dynamics of the flexible instrument containing the fiber sensor can be estimated.

In one embodiment, workstation 112 includes an image generation module 148 configured to receive feedback from the shape sensing device 104 and record real-time or accumulated position data as to where the sensing device 104 has been within a volume 131. An image 134 of the position data of the shape sensing device 104 within the space or volume 131 can be displayed on a display device 118. Workstation 112 includes the display 118 for viewing internal images of the subject (patient) or volume 131 and may include the image 134 as an overlay or other rendering of the history of visited positions of the sensing device 104. Display 118 may also permit a user to interact with the workstation 112 and its components and functions, or any other elements within the system 100. This is further facilitated by an interface 120 which may include a keyboard, mouse, a joystick, a haptic device, or any other peripheral or control to permit user feedback from and interaction with the workstation 112.

The shape sensing device 104 passes through a protective tube 210, a handle 212 and the instrument 102. In accordance with the present principles, the shape sensing device 104 is permitted to rotationally slip within the instrument 102 to control or limit rotation. The module 115 is configured to read measured twist in the shape sensing device 104. The handle 212 may include a rotary bearing 404 to mechanically isolate the protective tube 210 from instrument 102, and a clutch mechanism 402 for allowing rotation between the protective tube 210 and handle 212. A counter mechanism 406 may be included which counts a number of part/full rotations of the bearing 404. This information may be reported to the module 115/workstation 112 using a data link (e.g., cabling 127 or other communication link, e.g., wireless). Module 115 includes a twist measurement unit 152 that can use the number of twists as a trigger to perform a number of actions. For example, when the number of twists reaches a threshold, the twist measurement unit 152 engages the clutch mechanism 402 to limit rotation of the bearing 404.

The user interface 120 may optionally provide visual (e.g., on display 118) or audible feedback through speakers 122 to the operator about the state of the shape sensor 104 and/or instrument 102, especially with regard to a number of twists incurred thereon. Another illustrative embodiment will be described with respect to FIG. 2.

Figure 2:
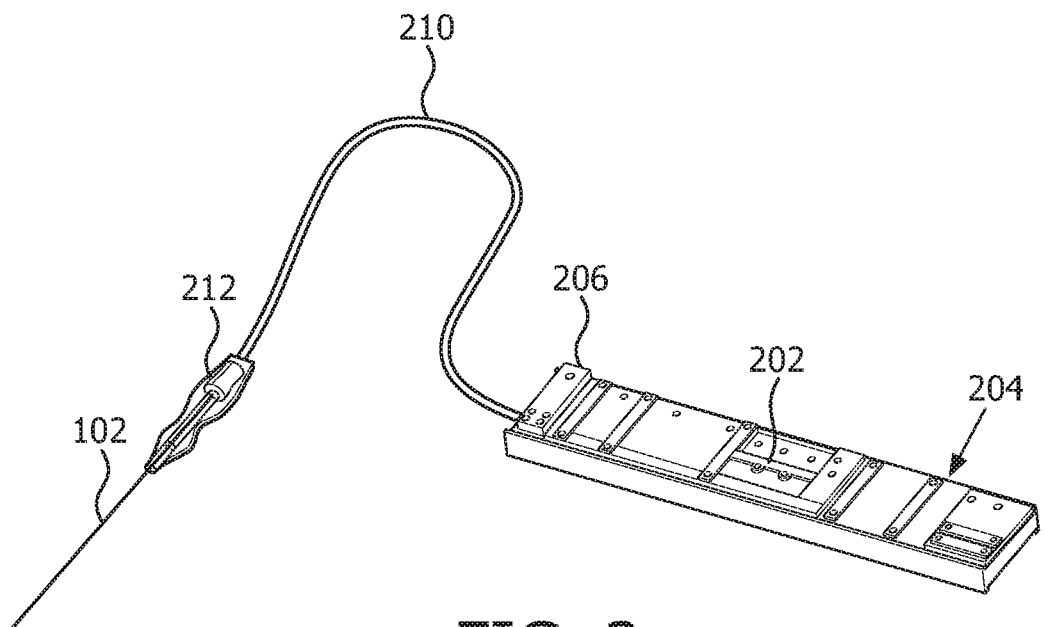
FIG. 2 is a perspective view of a shapes sensing system showing a launch unit, handle and medical instrument in accordance with one illustrative embodiment.

Referring to FIG. 2, the shape sensing device 104 (which is within the instrument 102 and not shown in FIG. 2) includes one or more an OSS fibers (not shown) which are provided inside a guide tube (not shown) within the instrument 102. The shape sensing device 104 includes shape sensing capabilities from a launch point or fixation point 202, which acts as the origin (0,0,0). The fixation point 202 is often located on a fixture or launch unit 204, which defines the frame of reference of the shape sensing device. The launch unit 204 may be incorporated into a workstation 112, as shown in FIG. 1, or may be a stand-alone unit. The launch unit 204 and/or workstation 112 include electronic and photonics devices for providing and receiving light for shape sensing applications.

After a guide tube fixation point 206, the shape sensing device 104 passes through a protective tube 210 and an instrument handle 212 to a distal tip of the instrument 102. The protective tube 210 is fixed at the guide tube fixation point 206 at the end of the launch unit 204 but can be configured to rotate at its distal end portion within the handle 212.

The instrument 102 includes the shape sensing device 104 inside of it, so the shape sensing device 104 is not shown. Normally, any rotation of the instrument induces twist in the fiber of the shape sensing device 104. However, in one embodiment, twisting of the fiber can be mitigated by mechanically isolating the fiber from the interventional instrument 102 such that the fiber is not fixed to the instrument 102 at any point along its length and does not rotate with the instrument 102 as a clinician rotates the handle 212 and/or the instrument 102. However, simply permitting the fiber to sit within a lumen is insufficient to ensure reconstruction stability due to torsional friction that would be applied to the fiber as the lumen rotates.

In accordance with one embodiment, the shape sensing device 104 also passes through a guide tube 304 (not shown) from the launch unit 204 through the instrument 102.

Figure 3:
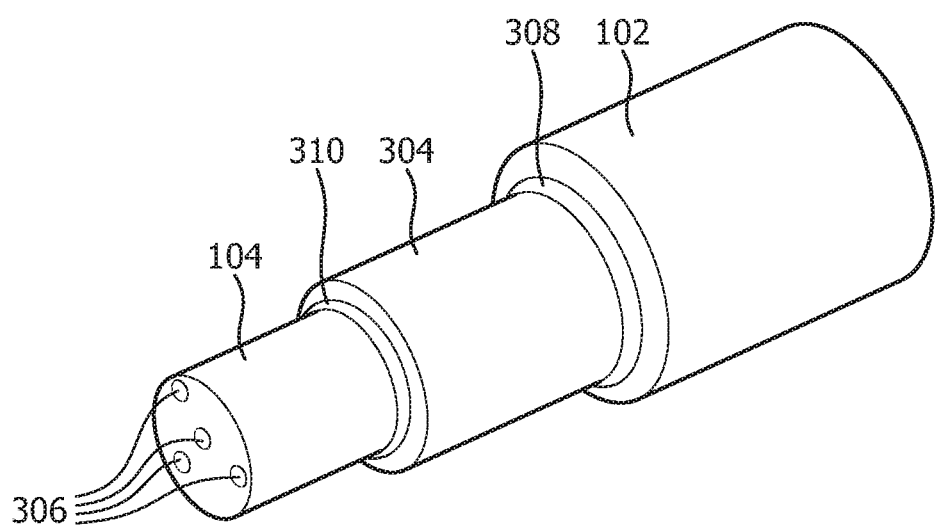
FIG. 3 is a cut-away perspective view showing a shape sensing device freely disposed in a guide tube which is freely disposed in an instrument in accordance with one illustrative embodiment.

Referring to FIG. 3, a close-up cut away view of the instrument 102 shows a guide tube 304 having the shape sensing device 104 disposed therein. The shape sensing device 104 may include one or more optical fibers 306. In one embodiment, the fibers 306 include a centrally disposed fiber surrounded by three even spaced outer fibers. In accordance with the present principles, a lumen or space 308 of the instrument 102 includes the guide tube 304. The guide tube 304 further includes a lumen or space 310, which permits the shape sensing device 104 to rotate freely therein.

Figure 4:
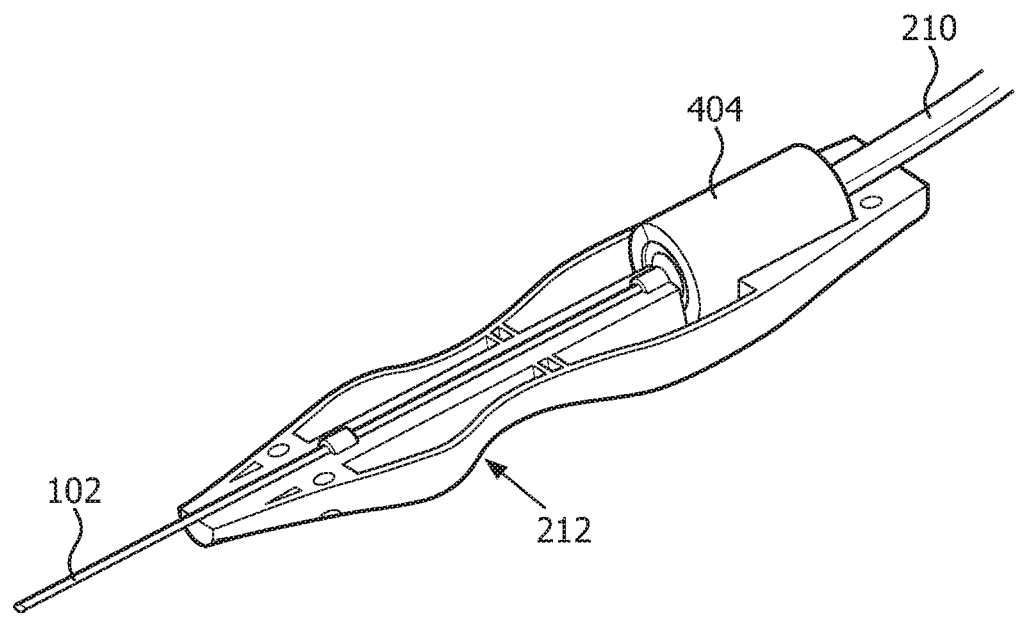
FIG. 4 is a perspective cut-away view of the handle (interface) in accordance with one illustrative embodiment.

Referring to FIG. 4, a cut-away perspective view of the device handle 212 is shown in accordance with one illustrative embodiment. The guide tube 304 (FIG. 3) passes through a lumen in the interventional instrument 102. The shape sensing device 104 (FIG. 3) within the guide tube 304 is fixed to the fiber launch unit 204 at the guide tube fixation point 206, which is distal from the fiber launch point 202 (as indicated in FIG. 2). The shape sensing device 104 is not fixed at any point in the guide tube 304 and the guide tube 304 is not fixed as it passes through the protective tubing 210 or the interventional instrument 102. The interventional instrument 102 is rigidly attached to the handle 212 such that any rotation of the handle 212 also rotates the instrument 102, but, in one embodiment, the protective tube 210 is free to slip relative to the instrument 102. The shape sensing device 104 is free to slip within the guide tube 304 and the guide tube is free to slip within the instrument 102.

A drawback of not fixing the OSS fiber (104) to the instrument 102 is that the orientation of the instrument tip is not directly sensed with the shape sensing device 104. In this situation, the roll along the longitudinal axis of the tip-section of the instrument can be estimated using software. A processing algorithm 156 (FIG. 1) within module 115 can exploit the known shape of the distal tip of the elongated device together with the OSS (x,y,z) shape measurements along the distal tip section. The known shape of the distal tip can be determined based on the pre-formed geometry imparted onto the tip section, or based on the deflection geometry imparted onto the distal tip by pull wires used for steering of the flexible instrument 102. The desired instrument tip orientation can be estimated using an optimization algorithm which computes the roll orientation angle that minimizes the difference between the measured shape and the known geometry according to a goodness-of-fit metric. This approach to estimating angular tip orientation can be used for any tip shape that is not rotationally symmetric e.g., a straight cylinder.

In particularly useful embodiments, the shape sensing device 104 is housed within the flexible guide tube 304, which passes through a lumen within the interventional instrument 102. The shape sensing device 104 is only fixed at the fiber fixation point 202 and the guide tube 304 is only fixed to the launch unit 204 at the guide tube fixation point 206 distal to the fiber fixation point 202. In such a configuration, both the guide tube 304 and the shape sensing device 104 are rotationally independent of the instrument 102. The interventional instrument 102 is rigidly attached to the handle 212 such that any rotation of the handle 212 rotates the instrument 102 about its longitudinal axis. The interventional instrument 102 may be rigidly fixed to the handle 212 by mechanical clamping, employing adhesives, etc. The guide tube 304 containing the shape sensing device 104 passes through the lumen in the interventional instrument 102 and is not fixed to the instrument at any point. Thus, when the handle 212 is rotated, the instrument 102 rotates, but the guide tube 304 and the shape sensing device 104 (fiber(s)) are free to slip relative to the rotation.

This rotation will cause friction between the wall of the guide tube 304 and the wall of the lumen (308, FIG. 3) within the instrument 102. However, the guide tube 304 should have sufficient torsional stiffness so as to slip relative to the lumen 308 of the instrument 102. In this scenario, the friction will not be transmitted to the shape sensing device 104 and hence the amount of twist experienced by the shape sensing device 104 will be minimized. In this configuration, the guide tube 304 can be considered a rotary bearing between the interventional instrument 102 and the shape sensing device 104.

In another embodiment, knowledge of a tip orientation may be needed for the instrument 102, and so it may be necessary to fix the shape sensing device 104 to a tip of the instrument 102. In this case, the use of a guide tube 304 as a rotary bearing may not be needed since the shape sensing device 104 needs to twist with the instrument 102. Additional features can be integrated into the handle 212 to reduce the likelihood of over-twisting the fiber. These may include the bearing 404 and the clutch 402, which may be employed in fixed fiber or non-fixed (free/slip) fiber embodiments.

Figure 5:
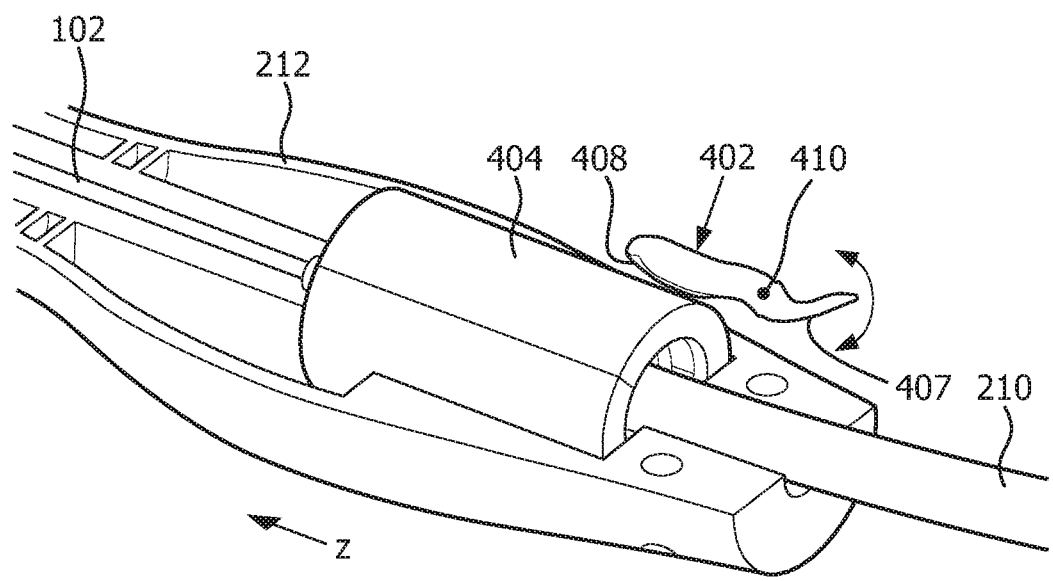
FIG. 5 is a magnified perspective cut-away view of the handle (interface) showing an illustrative clutch mechanism in accordance with one illustrative embodiment.

Referring to FIG. 5 with further reference to FIG. 2, between the device handle 212 and the launch unit 204, the shape sensing device 104 and guide tube 304 pass through the protective tubing 210 (FIG. 2). To protect the fiber in the shape sensing device 104 during normal use, the protective tube 210 should be torsionally stiff, incompressible, have a minimum bending radius and be clamped rigidly to the launch unit 204. If the protective tube 210 was also clamped rigidly to the handle 212, it would significantly restrict the range of motion that the instrument 102 can be rotated about the Z axis (parallel to the tube). This may be employed as a measure of twist control. However, to ensure that the clinician can rotate the handle 212 freely about this axis, the protective tube 210 and the handle 212 can be connected via a rotary bearing 404. This means that the clinician can control the orientation of the interventional instrument 102 without restriction from the protective tubing 210.

A clutch mechanism 402 is configured to clamp or release the bearing 404 which allows rotation between the shape sensing device 104 (which may be fixed within the instrument 102 or free to slip in the instrument 102/handle 212) and the instrument 102 and handle 212. The clutch 402 may be user-operated or computer controlled. The clutch 402 may include a frictional interface 408 against the bearing 404 using a pin fulcrum 410. The interface or engagement surface 408 may be controlled using a switch or lever 407. Other structures or configurations are also contemplated, e.g., an actuator that engages the bearings 404, etc.

If the clutch 402 is engaged, the bearing 404 is rigidly fixed to the handle 212 and the shape sensing device 104 would rotate with the instrument 102 and handle 212. Conversely, if the clutch 402 is disengaged, then the bearing 404 is free to rotate, and the handle 212 can be rotated relative to the protective tube 210. The rotary bearing 404 need not be limited to a device or handle 212 but may be made larger or smaller based on the application and used with other instruments or user interfaces such as guidewire torqueing devices, etc.

During some interventions, knowledge of the tip orientation is needed. For these, the fiber of the shape sensing device 104 needs to be fixed to the tip of the instrument 102. With such fixed tip instruments, the clinician should not over-twist the fiber and induce loss of tracking. In this scenario, the torsional stiffness of the protective tube 210 limits the amount of rotation the clinician could impart about the Z axis and thus would act as a safety feature to stop over-twisting of the instrument 102 during instrument setup prior to insertion in a body. If the clutch is disengaged, then the bearing is free to rotate.

Figure 6:
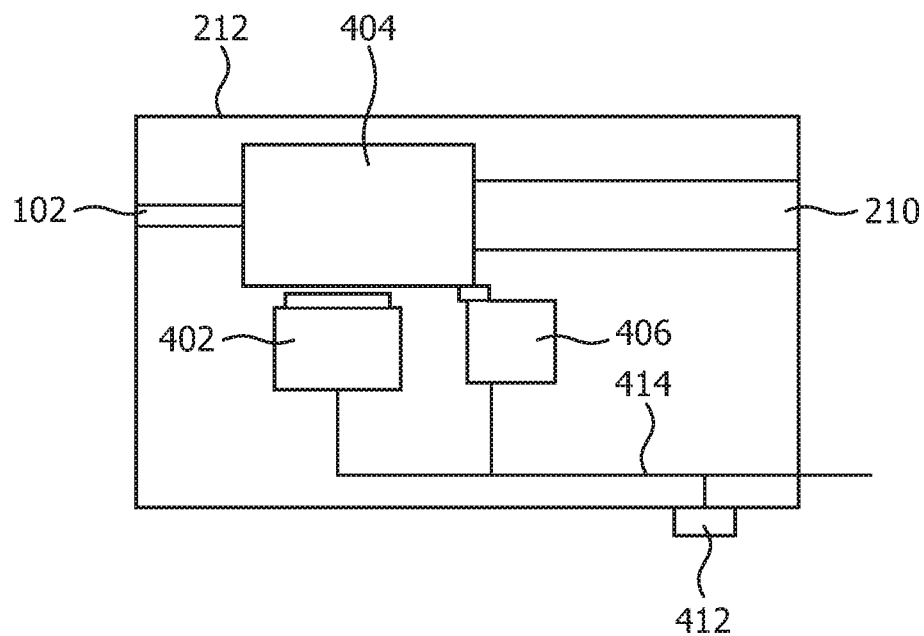
FIG. 6 is a schematic view of the handle (interface) showing another illustrative clutch mechanism using a counter and having a warning device in accordance with another illustrative embodiment.

Referring to FIG. 6, in one embodiment, automation of the clutch 402 (using, e.g., the workstation 112, FIG. 1) may include having the clutch 402 disengaged as a default but engaging the clutch 402 after insertion of the device into the body and while navigating through the anatomy, thus providing orientation information. The automation could also be provided by measuring the twist signal and using that as a criterion for engaging/disengaging the clutch 402. The clutch 402, shown in FIG. 6, 402 is an actuator that may be activated by the counter 406 or by the workstation 112 using signal (and/or power) leads 414.

The counter mechanism 406 may be provided which counts a number of full rotations of the bearing 404 when it is free to rotate. The counter 406 may include an encoder that measures a number of markings that pass, may include a mechanism that adds a count each time a protrusion is hit as the bearing 404 rotates, include a potentiometer, etc. When the number of rotations reaches a pre-defined limit or threshold (which is less than the amount of angular displacement the shape sensing device 104 can withstand), the mechanism 406 automatically engages the clutch 402 so that the clinician can no longer rotate the handle 212. This would indicate to the operator that the twist limit of the shape sensing device 104 is approaching. The operator could then take appropriate action by limiting rotation or untwisting the device. This would reduce the likelihood that the shape reconstruction goes unstable due to excessive twist. This may be robotically controlled as well.

Visual or audible indicators 412 can be employed to provide additional feedback to the operator. This would indicate to the operator that the twist limit of the shape sensing device 104 is approaching or has been exceeded. The operator could then take appropriate action by limiting rotation or untwisting. These features would reduce the likelihood that the shape reconstruction goes unstable due to excessive twist. The counter 406 may be employed as feedback to the module 115 to initiate the engagement of the clutch 402, which can be computer controlled (e.g., by module 115, FIG. 1).

Figure 7:
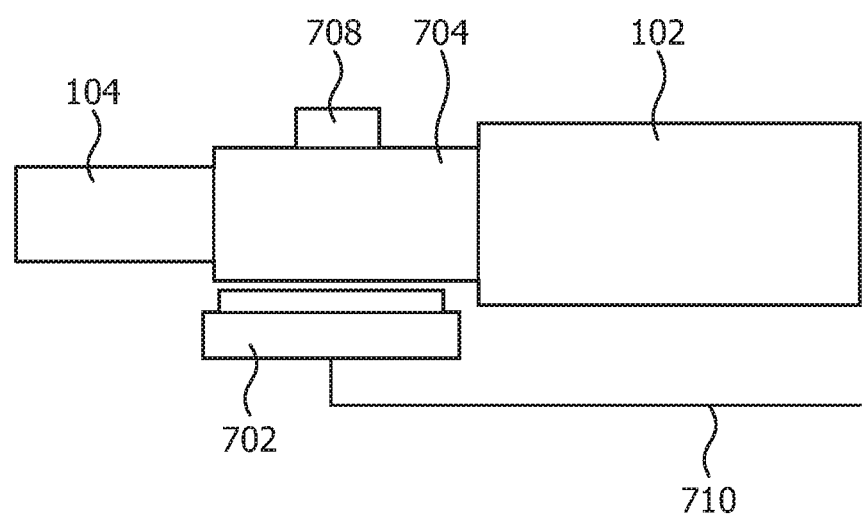
FIG. 7 is a schematic view of another illustrative clutch mechanism for fixing the shape sensing device to the instrument to enable a fixed or free shape sensing device in accordance with another illustrative embodiment.

Referring to FIG. 7, another clutch 702 may be employed to clamp or release a bearing 704 between the shape sensing device 104 and the instrument 102. The bearing 704 is attached to the shape sensing device 104. While the clutch 702 and bearing 704 may be implemented at any location within the instrument 104, it would be advantageous to place the clutch 702 and bearing 704 near a distal tip of the instrument and/or within the handle 212. An anvil 708 may be employed if a surface is needed to resist motion of the clutch 702. If the clutch 702 is engaged, the shape sensing device 104 is rigidly fixed to the handle 212 and the shape sensing device 104 would not rotate relative to the instrument 102. Conversely, if the clutch 702 is disengaged, the shape sensing device 104 would be free to rotate relative to the instrument 102. This permits a clinician to switch between operating the instrument 102 in a fixed tip or a floating tip configuration. The clutch 702 may be actuated and controlled by the workstation 112 through a signal line 710, or may include a manual control.

It should be understood that in other embodiments the shape sensing device may be manipulated by a robot or other intervening device. For example, twist may be introduced by a robotic manipulator which permits a clinician to teleoperate the shape sensing device. In such cases, the twist minimization methods disclosed would also be useful and advantageous.

In interpreting the appended claims, it should be understood that:
a) the word "comprising" does not exclude the presence of other elements or acts than those listed in a given claim;
b) the word "a" or "an" preceding an element does not exclude the presence of a plurality of such elements;
c) any reference signs in the claims do not limit their scope;
d) several "means" may be represented by the same item or hardware or software implemented structure or function; and
e) no specific sequence of acts is intended to be required unless specifically indicated.

Having described preferred embodiments for systems and methods for minimizing twist for optical shape sensing enabled instruments (which are intended to be illustrative and not limiting), it is noted that modifications and variations can be made by persons skilled in the art in light of the above teachings. It is therefore to be understood that changes may be made in the particular embodiments of the disclosure disclosed which are within the scope of the embodiments disclosed herein as outlined by the appended claims. Having thus described the details and particularity required by the patent laws, what is claimed and desired protected by Letters Patent is set forth in the appended claims.

The invention claimed is:

1. A shape sensing system, comprising:
a guide tube;
an optical shape sensing device including one or more optical fibers and being proximally fixed at a fixation point and being disposed within the guide tube; and
an interventional instrument rigidly attached to and extending distally from a handle to prevent rotation of the instrument relative to the handle, the instrument having a lumen configured to receive the guide tube therein such that the optical shape sensing device is unconstrained throughout the instrument and the handle in that the guide tube is free to slip relative to at least rotation of the instrument and the handle without transferring torsional friction to the optical shape sensing device;
wherein the handle includes a bearing to receive and attach to a protective tube extending proximally from the handle wherein the handle is free to rotate relative to the bearing and the protective tube, the protective tube encapsulating the optical shape sensing device between a fixation position at or near the fixation point and the handle, the optical shape sensing device being free to slip relative to rotation of the protective tube and the bearing.

2. The system as recited in claim 1, further comprising a counter configured to measure a number of rotations of the bearing.

3. A shape sensing system, comprising:
a guide tube;
an optical shape sensing device including one or more optical fibers and being proximally fixed at a fixation point and being disposed within the guide tube; and
an interventional instrument rigidly attached to a handle to prevent rotation of the instrument relative to the handle, the instrument having a lumen configured to receive the guide tube therein such that the optical shape sensing device is unconstrained throughout the instrument and the handle in that the guide tube is free to slip relative to at least rotation of the instrument and the handle without transferring torsional friction to the optical shape sensing device,
wherein the handle includes a bearing to receive and attach to a protective tube wherein the handle is free to rotate relative to the bearing and the protective tube, the protective tube encapsulating the optical shape sensing device between a fixation position at or near the fixation point and the handle, the optical shape sensing device being free to slip relative to rotation of the protective tube and the bearing, and further comprising a clutch configured to engage the bearing to prevent rotation of the handle relative to the protective tube.

4. The system as recited in claim 3, wherein the clutch is engaged when a number of rotations of the bearing reaches a threshold.

5. A shape sensing system, comprising:
a guide tube;
an optical shape sensing device including one or more optical fibers and being proximally fixed at a fixation point and being disposed within the guide tube;
an interventional instrument rigidly attached to a handle to prevent rotation of the instrument relative to the handle, the instrument having a lumen configured to receive the guide tube therein such that the optical shape sensing device is unconstrained throughout the instrument and the handle in that the guide tube is free to slip relative to at least rotation of the instrument and the handle without transferring torsional friction to the optical shape sensing device,
wherein the handle includes a bearing to receive and attach to a protective tube wherein the handle is free to rotate relative to the bearing and the protective tube, the protective tube encapsulating the optical shape sensing device between a fixation position at or near the fixation point and the handle, the optical shape sensing device being free to slip relative to rotation of the protective tube and the bearing,
further comprising a counter configured to measure a number of rotations of the bearing and a warning mechanism configured to provide a sensory warning to an operator based on a number of rotations of the bearing.

6. A shape sensing system, comprising:
a guide tube;
an optical shape sensing device including one or more optical fibers and being proximally fixed at a fixation point and being disposed within the guide tube; and
an interventional instrument rigidly attached to a handle to prevent rotation of the instrument relative to the handle, the instrument having a lumen configured to receive the guide tube therein such that the optical shape sensing device is unconstrained throughout the instrument and the handle in that the guide tube is free to slip relative to at least rotation of the instrument and the handle without transferring torsional friction to the optical shape sensing device,
further comprising a user controlled clutch configured to engage a bearing attached to the shape sensing device in order to constrain relative rotation between the optical fiber sensing device and the instrument.

7. A shape sensing system, comprising:
a workstation including a processor and memory, the memory storing a shape sensing module configured to interpret optical shape sensing signals during an interventional procedure;
a launch unit including an optical fixation point for sending and receiving optical signals;
a guide tube being proximally fixed at a mount point distally disposed from the fixation point;
an optical shape sensing device including one or more optical fibers and being proximally fixed at the fixation point and being disposed within the guide tube; and an interventional instrument rigidly attached to and distally extending from a handle to prevent rotation of the instrument relative to the handle, the instrument having a lumen configured to receive the guide tube therein such that the optical shape sensing device is unconstrained throughout the instrument and the handle in that the guide tube is free to slip relative to at least rotation of the instrument and the handle without transferring torsional friction to optical shape sensing device;
wherein the handle includes a bearing to receive and attach to a protective tube extending proximally from the handle wherein the handle is free to rotate relative to the bearing and the protective tube, the protective tube encapsulating the optical shape sensing device between the mount point and the handle, the optical shape sensing device being free to slip relative to rotation of the protective tube and the bearing.

8. The system as recited in claim 7, further comprising a counter configured to measure a number of rotations of the bearing.

9. A shape sensing system, comprising:
a workstation including a processor and memory, the memory storing a shape sensing module configured to interpret optical shape sensing signals during an interventional procedure;
a launch unit including an optical fixation point for sending and receiving optical signals;
a guide tube being proximally fixed at a mount point distally disposed from the fixation point;
an optical shape sensing device including one or more optical fibers and being proximally fixed at the fixation point and being disposed within the guide tube;
an interventional instrument rigidly attached to a handle to prevent rotation of the instrument relative to the handle, the instrument having a lumen configured to receive the guide tube therein such that the optical shape sensing device is unconstrained throughout the instrument and the handle in that the guide tube is free to slip relative to at least rotation of the instrument and the handle without transferring torsional friction to optical shape sensing device; and
wherein the handle includes a bearing to receive and attach to a protective tube wherein the handle is free to rotate relative to the bearing and the protective tube, the protective tube encapsulating the optical shape sensing device between the mount point and the handle, the optical shape sensing device being free to slip relative to rotation of the protective tube and the bearing,
further comprising a clutch configured to engage the bearing to prevent rotation of the handle relative to the protective tube.

10. The system as recited in claim 9, wherein the clutch is engaged when a number of rotations of the bearing reaches a threshold.

11. A shape sensing system comprising:
a workstation including a processor and memory, the memory storing a shape sensing module configured to interpret optical shape sensing signals during an interventional procedure;
a launch unit including an optical fixation point for sending and receiving optical signals;
a guide tube being proximally fixed at a mount point distally disposed from the fixation point;
an optical shape sensing device including one or more optical fibers and being proximally fixed at the fixation point and being disposed within the guide tube;

an interventional instrument rigidly attached to a handle to prevent rotation of the instrument relative to the handle, the instrument having a lumen configured to receive the guide tube therein such that the optical shape sensing device is unconstrained throughout the instrument and the handle in that the guide tube is free to slip relative to at least rotation of the instrument and the handle without transferring torsional friction to optical shape sensing device; and wherein the handle includes a bearing to receive and attach to a protective tube wherein the handle is free to rotate relative to the bearing and the protective tube, the protective tube encapsulating the optical shape sensing device between the mount point and the handle, the optical shape sensing device being free to slip relative to rotation of the protective tube and the bearing, further comprising a counter configured to measure a number of rotations of the bearing, and further comprising a warning mechanism configured to provide a sensory warning to an operator based on a number of rotations of the bearing.

12. A shape sensing system, comprising:

a workstation including a processor and memory, the memory storing a shape sensing module configured to interpret optical shape sensing signals during an interventional procedure;

a launch unit including an optical fixation point for sending and receiving optical signals;

a guide tube being proximally fixed at a mount point distally disposed from the fixation point;

an optical shape sensing device including one or more optical fibers and being proximally fixed at the fixation point and being disposed within the guide tube; and an interventional instrument rigidly attached to a handle to prevent rotation of the instrument relative to the handle, the instrument having a lumen configured to receive the guide tube therein such that the optical shape sensing device is unconstrained throughout the instrument and the handle in that the guide tube is free to slip relative to at least rotation of the instrument and the handle without transferring torsional friction to optical shape sensing device, further comprising a user controlled clutch configured to engage a bearing attached to the shape sensing device in order to constrain relative rotation between the optical fiber sensing device and the instrument.

13. A shape sensing system, comprising:

an optical shape sensing device including one or more optical fibers and being proximally fixed at a fixation point; and an interventional instrument rigidly attached to a handle to prevent rotation of the instrument relative to the handle, the instrument having a lumen configured to receive the optical shape sensing device;

a bearing included in the handle and configured to receive and attach to a protective tube wherein the handle is free to rotate relative to the bearing and the protective tube, the protective tube encapsulating the optical shape sensing device between a fixation position, at or near the fixation point, and the handle; and a clutch configured to engage the bearing to prevent rotation of the handle relative to the protective tube in accordance with an event.

* * * * *